United States Patent
Schaack

[11] Patent Number: 6,121,999
[45] Date of Patent: Sep. 19, 2000

[54] ELIMINATING ROUTINE ALIGNMENT CALIBRATIONS IN PERSPECTIVE DIMENSIONAL MEASUREMENTS

[76] Inventor: David F. Schaack, 11719 Menaul Blvd., Suite C, Albuquerque, N. Mex. 87112-2419

[21] Appl. No.: 08/871,289

[22] Filed: Jun. 9, 1997

[51] Int. Cl.[7] ...................................................... A61B 1/04
[52] U.S. Cl. ............................... 348/45; 348/49; 348/82; 348/135; 702/127; 359/691
[58] Field of Search .................. 348/45, 46, 47, 348/48, 49, 61, 62, 65, 348, 357, 82, 83, 84, 85, 135, 142; 600/167, 117; 385/117; 356/241; 359/691; 128/4, 107; 358/98; 702/127, 155, 156, 159, 151–153; A61B 1/04

[56] References Cited

U.S. PATENT DOCUMENTS

| | | | |
|---|---|---|---|
| 4,207,594 | 6/1980 | Morris et al. | 358/107 |
| 4,941,106 | 7/1990 | Krieger | 364/513 |
| 4,980,763 | 12/1990 | Lia | 358/98 |
| 5,070,401 | 12/1991 | Salvati et al. | 348/135 |
| 5,191,879 | 3/1993 | Krauter | 128/4 |
| 5,214,538 | 5/1993 | Lobb | 359/691 |
| 5,573,492 | 11/1996 | Dianna et al. | 600/117 |
| 5,669,871 | 9/1997 | Sakiyama | 600/117 |
| 5,704,897 | 1/1998 | Truppe | 600/117 |
| 5,801,762 | 9/1998 | Dianna et al. | 348/65 |
| 5,817,019 | 10/1998 | Kawashima | 600/437 |
| 6,009,189 | 12/1999 | Schack | 382/154 |

*Primary Examiner*—Vu Le
*Assistant Examiner*—Tung Vo
*Attorney, Agent, or Firm*—Michael J. Tavella

[57] ABSTRACT

An improved system of perspective dimensional measurement uses complementary reference surfaces on a camera and on a camera translating unit to provide a repeatable relative orientation between the perspective displacement and the camera's measurement coordinate system while still allowing a rotational and an optional translational degree of freedom for alignment of the camera with an object of interest. In one set of embodiments the rotational axis is accurately aligned with the translation axis. In a second set of embodiments, the geometry of the system is determined in an expanded alignment calibration procedure, the rotation of the camera about the rotational axis is measured, and these additional data are incorporated into the perspective measurement procedure.

15 Claims, 11 Drawing Sheets

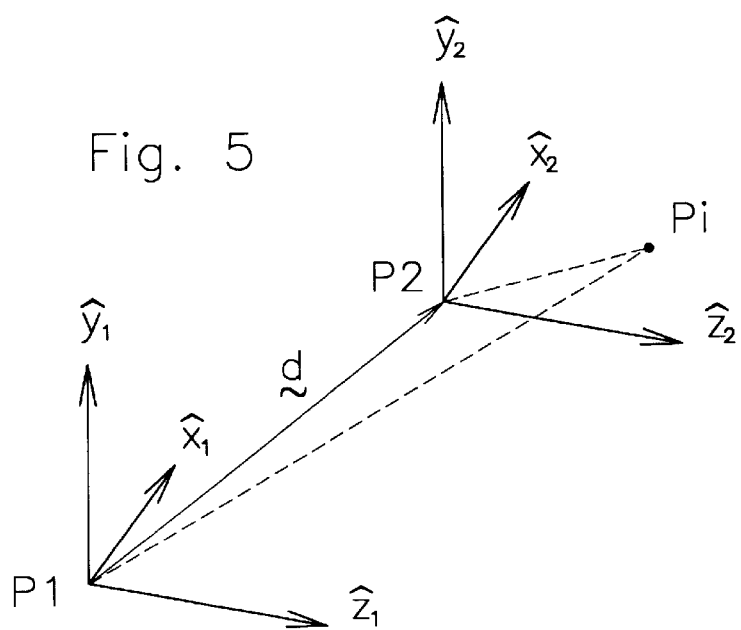
Fig. 5
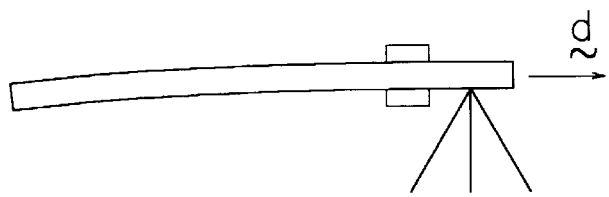
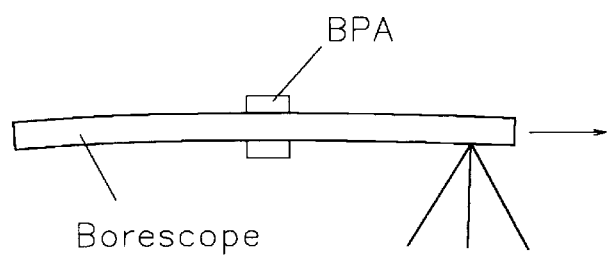
Fig. 6
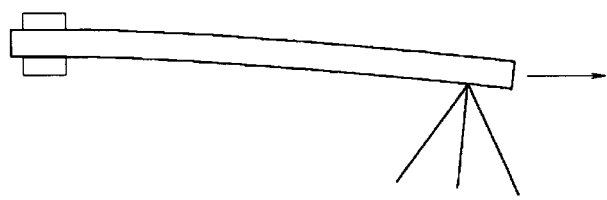

ELIMINATING ROUTINE ALIGNMENT CALIBRATIONS IN PERSPECTIVE DIMENSIONAL MEASUREMENTS

FIELD OF THE INVENTION

This invention relates to optical metrology, especially to the problem of making accurate non-contact dimensional measurements of objects which are viewed through an endoscope.

BACKGROUND

In the past several decades, the use of optical endoscopes has become common for the visual inspection of inaccessible objects, such as the internal organs of the human body or the internal parts of machinery. These visual inspections are performed in order to assess the need for surgery or equipment tear down and repair; thus the results of the inspections are accorded a great deal of importance. Accordingly, there has been much effort to improve the art in the field of endoscopes.

Endoscopes are long and narrow optical systems, typically circular in cross-section, which can be inserted through a small opening in an enclosure to give a view of the interior. They almost always include a source of illumination which is conducted along the interior of the scope from the outside (proximal) end to the inside (distal) end, so that the interior of a chamber can be viewed even if it contains no illumination. Endoscopes come in two basic types; these are the flexible endoscopes (fiberscopes and videoscopes) and the rigid borescopes. Flexible scopes are more versatile, but borescopes can provide higher image quality, are less expensive, are easier to manipulate, and are thus generally preferred in those applications for which they are suited.

While endoscopes (both flexible and rigid) can give the user a relatively clear view of an inaccessible region, there is no inherent ability for the user to make a quantitative measurement of the size of the objects he or she is viewing. There are many applications for which the size of an object, such as a tumor in a human body, or a crack in a machine part, is a critically important piece of information. Making a truly accurate measurement under these circumstances is a long-standing problem that has not been adequately dealt with until recently.

In my application, Ser. No. 08/689,993, now U.S. Pat. No. 6,009,189 entitled "Apparatus And Method For Making Accurate Three-Dimensional Size Measurements Of Inaccessible Objects", filed Aug. 16, 1996, and which is incorporated herein by reference, I teach a complete system for making measurements of objects viewed through endoscopes. With this system, it is for the first time possible to make measurements which are truly accurate in endoscopic applications. What I mean by "truly accurate" is that the level of accuracy is limited only by the technology of mechanical metrology and by unavoidable errors made by the most careful user.

My system also offers the user the capability to make a usefully accurate measurement at low cost. By "usefully accurate", I mean that the accuracy of the measurement is adequate for the purposes of most common industrial applications. By "low cost", I mean that the user can add this measurement capability to his or her existing remote visual inspection capability with a lower incremental expenditure than is required with previously available systems.

I call this new method "perspective dimensional measurement". By "perspective" I am referring to the use of two or more views of an object, obtained from different viewing positions, for dimensional measurement of the object. By "dimensional measurement", I mean the determination of the true three-dimensional (height, width, and depth) distance between two or more selected points on the object.

To perform a perspective dimensional measurement, the apparent positions of each of the selected points on the object are determined in each of the views. This is the same principle used in stereoscopic viewing, but here one is concerned with making quantitative measurements of object dimensions, rather than obtaining a view of the object containing qualitative depth cues. As I taught in the referenced patent application, given sufficient knowledge about the relative locations, orientations and imaging properties of the viewing optical system(s) or camera(s), one can determine the locations of the selected points in a measurement coordinate system. Once these locations are known, one then simply calculates the desired distances between the selected points by use of the well-known Pythagorean Theorem.

As a necessary and integral part of my complete measurement system, I taught how to calibrate it in the referenced co-pending application. I taught the use of a complete set of robust calibration procedures, which removes the need for the measurement system to be built accurately to a specific geometry, and also removes any need for the camera (s) to be built accurately to specific optical characteristics. Instead, I taught how to calibrate the geometry of the opto-mechanical hardware, and how to take that actual geometry into account in the measurement process. The complete set of calibration procedures I taught includes three different types of calibration. In optical calibration, the characteristics of each camera, when used as a precision image forming device, are correctly determined. In alignment calibration, the orientation of each camera's measurement coordinate axes with respect to the translation of the camera are determined. Finally, in motion calibration, any errors in the actual motion of the camera(s), as compared to the ideal motion, are determined.

In certain embodiments, my system of perspective dimensional measurement, as taught in the referenced co-pending application, enables one to make accurate measurements using a standard, substantially side-looking, rigid borescope. Since the person who needs the measurement will often already own such a borescope, the new method has a significant cost advantage over previous measurement techniques.

In a preferred set of embodiments, the motion of the borescope is constrained to lie along a substantially straight line. The borescope is supported by and its position is controlled by a mechanical assembly that I call the borescope positioning assembly (BPA). The borescope is attached to the BPA with a clamp which allows the borescope to slide and rotate with respect to the BPA so that the user may conveniently acquire the object of interest in the borescope's field of view. Once the object is acquired, the clamp is tightened to securely attach the borescope to the BPA, and then the measurement can proceed.

While these embodiments produce accurate dimensional measurements using a standard borescope, there is a difficulty. The problem is that a new alignment calibration may have to be performed each time a new measurement situation is set up. In alignment calibration, the orientation of the borescope's measurement coordinate axes with respect to the motion provided by the BPA is determined. With a standard borescope, this orientation may not be well controlled, and thus every time the borescope is repositioned with respect to the BPA, there is the logical requirement for a new alignment calibration. Of course, whether a new calibration would actually be required in any specific instance depends on the accuracy required of the dimensional measurement in that instance.

SUMMARY OF THE INVENTION

It is a first object of this invention to provide an apparatus and method that enables accurate perspective measurements to be made with a rigid borescope without requiring more than an occasional alignment calibration, while still allowing the user to rotate and slide the borescope with respect to the BPA for convenient acquisition of the object of interest into the field of view of the borescope.

It is a second object of this invention to provide a method which allows accurate perspective measurements to be made with any single camera, linear motion embodiment of my perspective measurement system where the camera is also allowed to rotate about an axis of rotation for convenient acquisition of objects of interest, where that axis of rotation is not aligned with the direction of linear camera motion, and where this rotational motion is made prior to (and not during) the perspective measurement process.

Accordingly, certain modifications are made to the borescope, to the BPA, and to the calibration and measurement procedures which work together to eliminate the need for routine alignment calibrations in borescope/BPA embodiments of the perspective measurement system. An improved borescope/BPA embodiment combines one of the following modifications of the borescope with one of the subsequently described modifications of the BPA and procedures.

The borescope is modified to include a suitable precision mounting reference surface. In one modification, the reference surface is a calibration sleeve or metrology sleeve which has an outer surface that has been fabricated accurately circular and straight. The calibration sleeve, when firmly attached to the borescope, eliminates alignment errors caused by the uncontrolled geometry of the standard borescope. As long as the calibration sleeve remains fixed at the same position with respect to the borescope, a single alignment calibration will serve for all of the measurements made with that scope. A second possible borescope modification defines a metrology borescope. A metrology borescope has a lens tube envelope that is stiffer than usual, and is fabricated so that its outer surface is accurately circular and straight, thereby acting as the mounting reference surface.

The BPA is modified so as to better characterize its borescope mounting reference surface. In one modification, the reference surface of the BPA is arranged to be in accurate alignment with the translation of the BPA, either through adjustment or by accurate fabrication. In a second possible modification, the rotational orientation of the borescope with respect to the BPA is determined as part of the measurement, and the alignment of the reference surface of the BPA with respect to the translation it produces is determined in an expanded alignment calibration procedure. These additional data are then incorporated into the perspective measurement process to produce an accurate measurement.

For the general single camera, linear motion embodiment of the perspective measurement system, the improvement consists of measurement of the rotational orientation of the camera about the axis of rotation and incorporation of this rotational measurement, together with the orientation of the axis of rotation with respect to the camera translation as determined in an expanded alignment calibration, to produce an accurate perspective measurement in the presence of this camera rotation.

Further objects and advantages of my improved system will become apparent from a consideration of the drawing and ensuing description.

BRIEF DESCRIPTION OF THE DRAWING

FIG. 5 shows the relationship between two visual coordinate systems and a point of interest.

FIG. 6 represents an example of the change in alignment between a perspective displacement vector, $\bar{d}$, and a borescope's visual coordinate system that can occur if the borescope lens tube is not straight.

FIG. 8A is a perspective view of an embodiment of a strain-relieving calibration sleeve.

DETAILED DESCRIPTION

A. Explanation of the Problem

Figure 1:
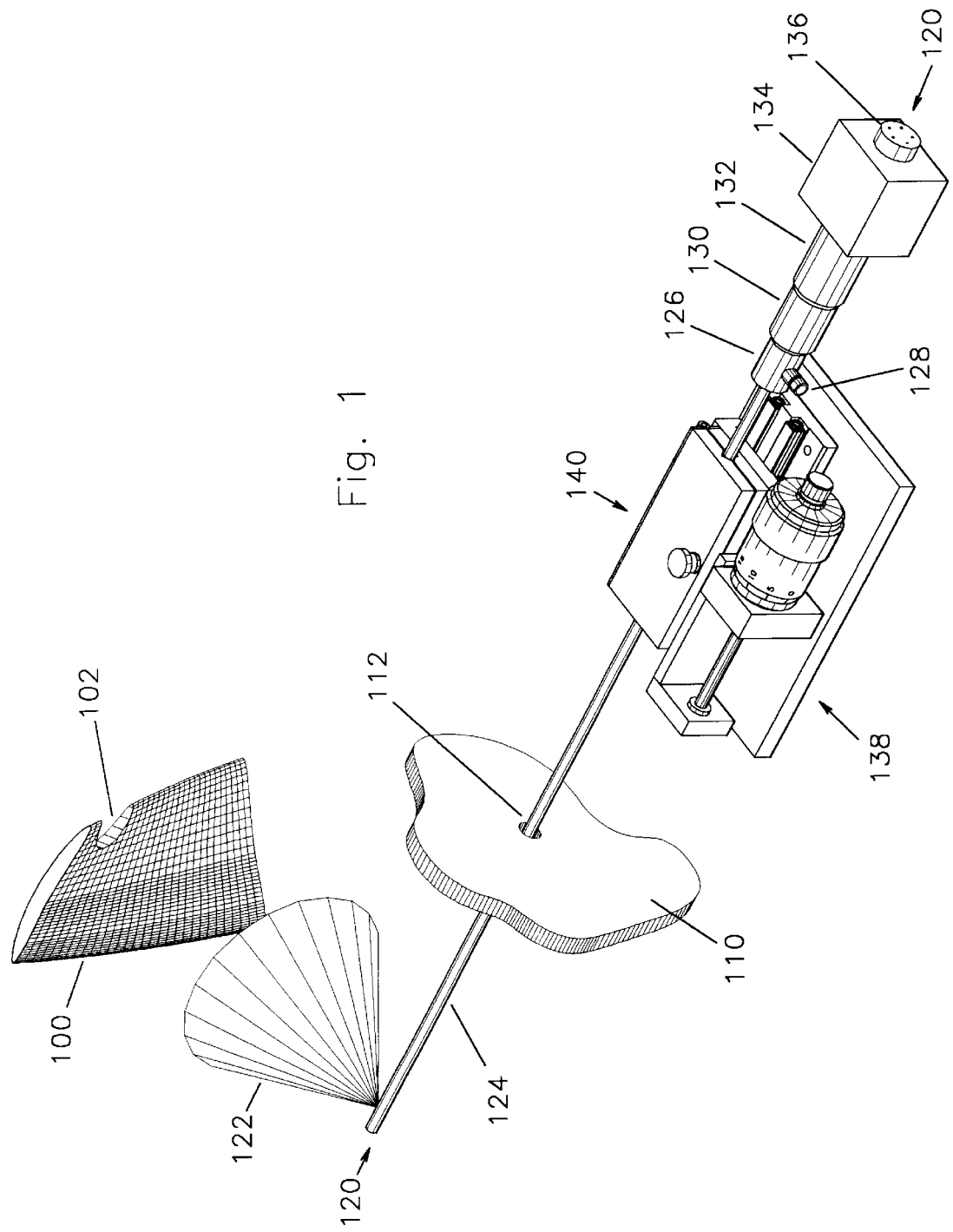
FIG. 1 is a perspective view of the mechanical portion of an embodiment of my perspective dimensional measurement system and its use in a typical situation.

FIG. 1 shows a standard rigid video borescope viewing an object of interest. The borescope is being supported by a borescope positioning assembly, which was described as one embodiment of the mechanical portion of the perspective dimensional measurement system as fully disclosed in the aforementioned co-pending application. A somewhat detailed description of this structure and of the perspective measurement method will now be given to aid the reader in understanding the problem solved by the improved system of the present invention.

In FIG. 1, an object 100 with a damaged area or feature of interest 102 is being viewed with a video borescope system 120. The configuration of video borescope system 120 shown is meant to be generic, and should not be construed as defining a specific video borescope to be used with my invention.

Object 100 is completely enclosed by an enclosure 110. In FIG. 1 only a small portion of the wall of enclosure 110 is shown. The borescope has been inserted through an inspection port 112 in the wall of enclosure 110. The borescope is supported by and its position is controlled by a borescope positioning assembly (BPA) 138. The configuration of BPA 138 shown here is also meant to be generic, and should not be construed to limit the applicability of the present invention to alternate embodiments such as those disclosed in the referenced co-pending application.

Conical field of view 122 represents the angular extent of the field visible through the borescope. A small diameter, elongated lens tube 124 comprises the largest portion of the length of the borescope. The remainder of the borescope is comprised successively of an illumination interface adapter 126, a focusing ring 130, a video adapter 132, and a video camera back or video sensor 134. Video camera back 134 represents every element of a closed circuit television camera, except for the lens. Video adapter 132 acts to optically couple the image formed by the borescope onto the image sensing element of video camera back 134 as well as serving as a mechanical coupling.

Illumination adapter 126 provides for the connection of an illumination fiber optic cable (not shown) to the borescope through a fiber optic connector 128. The illumination (not shown) exits lens tube 124 near the apex of field of view cone 122 to illuminate objects contained within cone 122.

A camera connector 136 connects video camera back 134 to its controller (not shown) through a cable which is also not shown. The video signal from camera back 134 is displayed on a video monitor which is not shown.

The portion of BPA 138 which directly supports the borescope is a clamp assembly 140, which clamps lens tube 124 at any convenient position along its length, thereby supporting the weight of borescope 120 and determining its position and orientation. BPA 138 is itself supported by a structure which is attached to enclosure 110 or to some other structure which is fixed in position with respect to object 100. This support structure is not shown, and is not relevant to the present invention.

Figure 2:
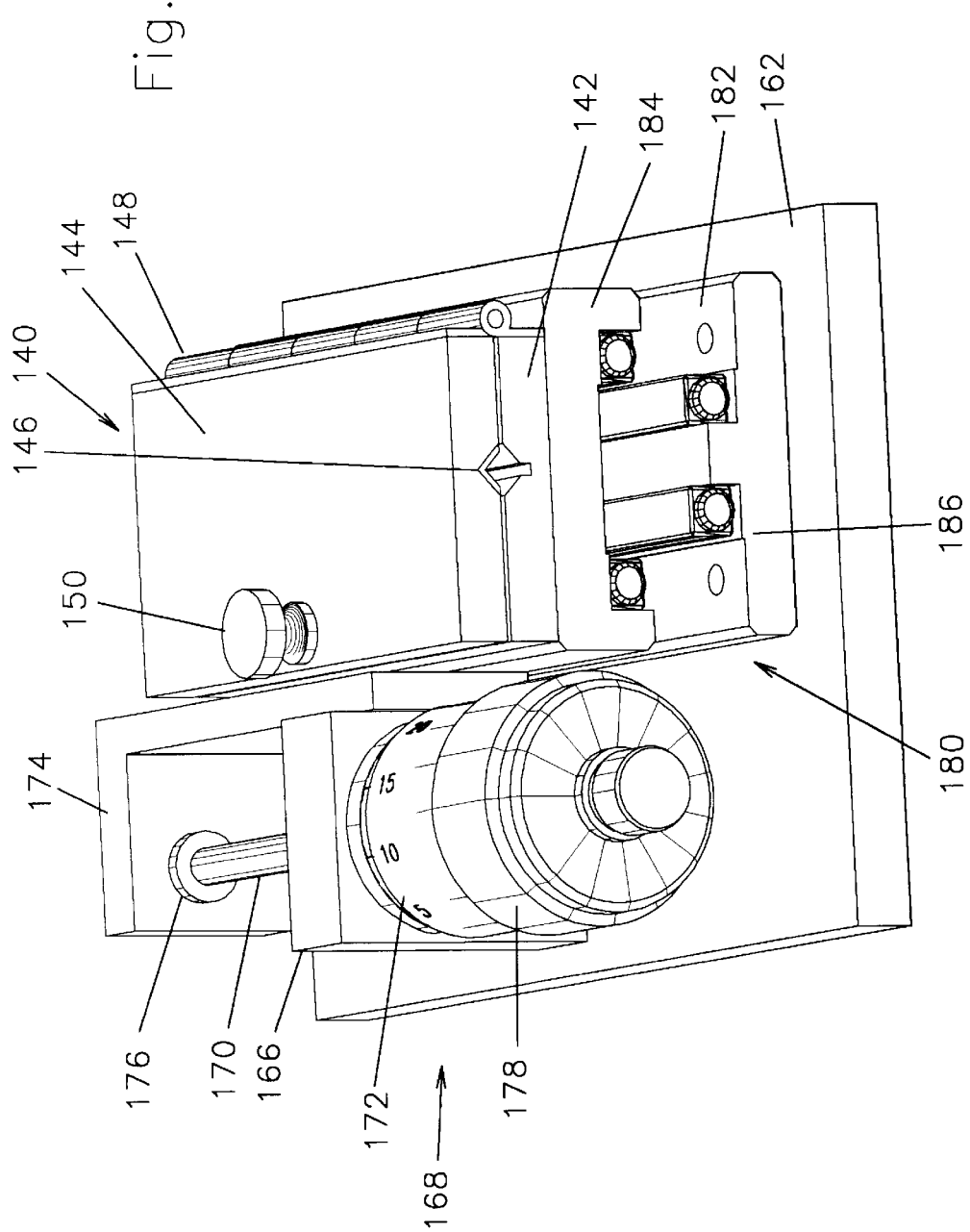
FIG. 2 is a close-up perspective view of the borescope positioning assembly (BPA).

BPA 138 is shown in more detail in FIG. 2. Lens tube 124 has been removed from clamp 140 in this view for clarity. Clamp 140 is comprised of a lower V—block 142, an upper V—block 144, a hinge 148, and a clamping screw 150. The upper V—block is lined with a layer of resilient material 146, in order that the clamping pressure on lens tube 124 can be evenly distributed over a substantial length of the tube.

Lower V—block 142 is attached to moving table 184 of a translation stage or slide table 180. Translation stage 180 is a standard component commercially available from several vendors, and it provides for a smooth motion of moving table 184 which is precisely constrained to a straight line. Translation stage 180 consists of moving table 184 and a fixed base 182, connected by crossed roller bearing slides 186. Fixed base 182 is attached to a BPA baseplate 162.

Also attached to BPA baseplate 162 is a micrometer mounting block 166. Mounting block 166 supports a micrometer 168. Micrometer 168 has an extension shaft 170, a rotating drum 178, and a distance scale 172. As drum 178 is rotated, a precision screw inside the micrometer rotates inside a precision nut, thus changing the distance between the end of extension shaft 170 and mounting block 166.

Micrometer extension shaft 170 is connected to an actuator arm 174 through a bushing 176. Actuator arm 174 is mounted to moving table 184. Micrometer scale 172 can be read to determine the position of moving table 184 within its range of motion.

Figure 3:
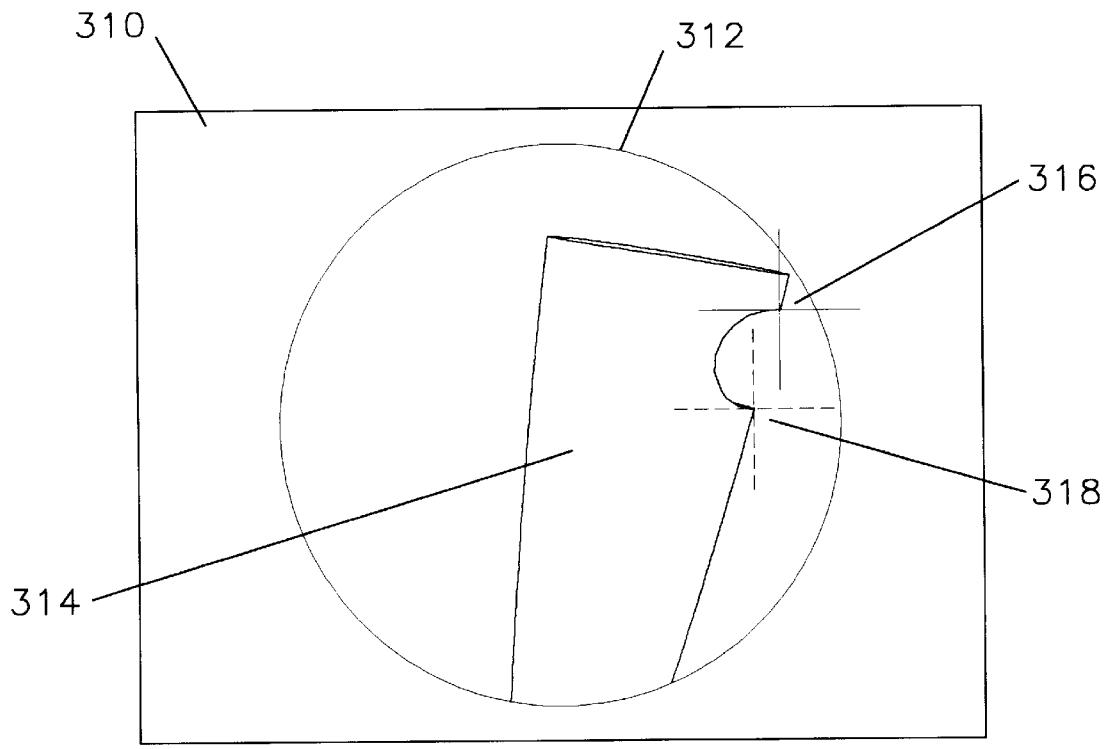
FIG. 3 is a view of the video monitor as seen by a user during a first stage of a perspective measurement procedure.

FIG. 3 shows a view of the video monitor as seen by the user. On video screen 310 there is seen a circular image of the borescope field of view, which I call the apparent field of view, 312. Inside apparent field of view 312 is shown an image of the object under inspection 314. Superimposed on video screen 310, and hence on image 314, are a pair of cross-hairs, fiducial marks, or cursors, 316 and 318. These cursors can be moved to any portion of the video screen, and can be adjusted in length, brightness, and line type as required for best alignment with points of interest on image 314. The video horizontal and vertical directions, together with the optical axis of the borescope, form a visual coordinate System in which measurements are made.

The perspective measurement of the distance across an object feature requires that the user first locate the object of interest in apparent field of view 312 by moving video borescope 120 back and forth and rotating it about its long axis inside loosened clamp 140. Once the object is located, clamp 140 is tightened and further adjustments of the position of image of the object 314 are made using micrometer 168.

Figure 4:
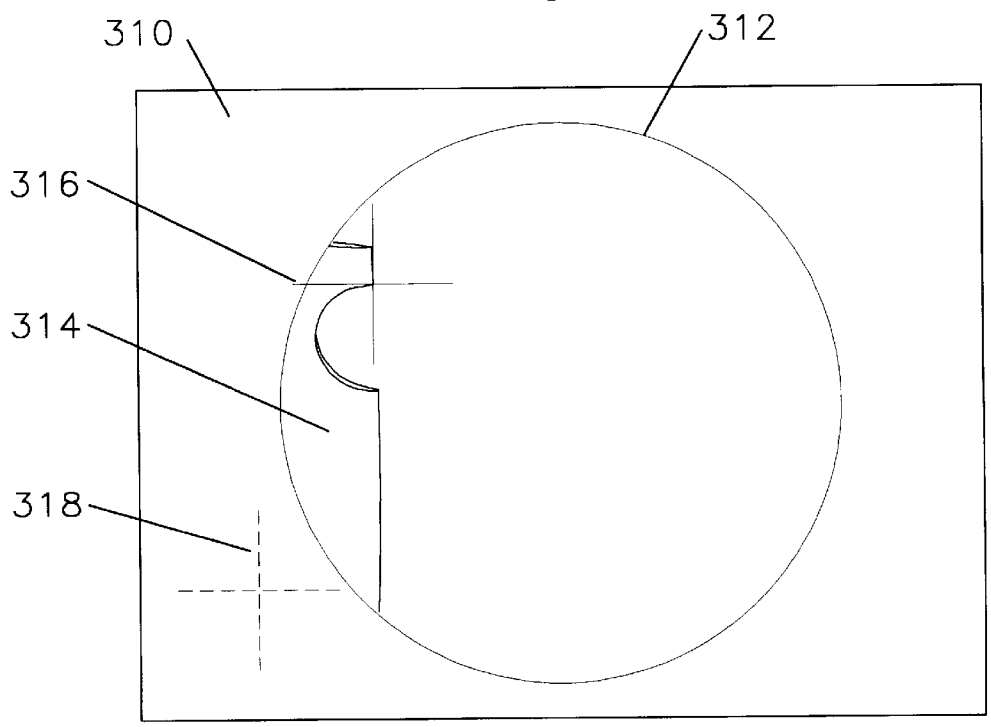
FIG. 4 is a view of the video monitor as seen by a user during a second stage of a perspective measurement procedure.

To begin the measurement process. the user superimposes cursors 316 and 318 on the video images of the object points of interest, with the image of the object offset to one side of apparent field of view 312, just as shown in FIG. 3. The positions of cursors 316 and 318 and the reading of micrometer scale 172 are then recorded. After these data are acquired, the user rotates drum 178 of micrometer 168 so that borescope 120 is physically translated along a precise straight line by a known distance. The user performs this translation until the object points of interest are located substantially on the opposite side of the apparent field of view, as shown in FIG. 4. After the user has performed this step, once again the apparent locations of the object points of interest are located with the video cursors and the micrometer is read.

It is shown in the referenced co-pending application that these experimental data, which consist of four image position coordinates for each object point of interest and the reading of the micrometer at each of the two viewing positions, are enough information to determine the true three-dimensional distance between the selected object points, provided that certain calibrations of the system have been accomplished.

In optical calibration, the detailed characteristics of the borescope, when used as a precision image forming device, are determined. In alignment calibration, the orientation of the visual coordinate system with respect to the straight line translation is determined. Since the improvements of the present invention are concerned primarily with the maintenance of this orientation or alignment, it will now be described in more detail.

As shown in FIG. 5, in the perspective measurement process the object of interest is viewed from two points in space, which may be called P1 and P2. At each viewing position, the apparent angular location of a point of interest, $P_i$, is determined in a visual coordinate system at that viewing position. The visual coordinate systems are defined by the horizontal and vertical video directions (x and y) and the optical axis of the borescope (z). At each viewing position, the origin of the visual coordinate system is taken to be at the nodal point of the borescope optical system. If the motion of the borescope from viewing position P1 to viewing position P2 is a pure translation, then the visual coordinate system at P1 ($x_1$, $y_1$, $z_1$) is oriented parallel to the visual coordinate system at P2 ($x_2$, $y_2$, $z_2$).

The vector connecting the nodal point of the borescope at viewing position P1 to the nodal point of the borescope at viewing position P2 is defined as the perspective displacement, $\overline{d}$. The essence of alignment calibration is to determine the orientation of the perspective displacement with respect to the visual coordinate systems. If these two coordinate systems are parallel, then $\overline{d}$ has the same orientation with respect to either one, and one can speak of the orientation of $\overline{d}$ with respect to the visual coordinate system. (In the referenced co-pending application, it was shown how to make the measurement in the case where the visual coordinate systems at P1 and P2 are not parallel. The improvements being disclosed here are applicable in that case as well, but further discussion of that case would simply add needless complication here.)

To begin the calculations necessary, to the perspective measurement, the tangents of the angles at which a point of interest is viewed with respect to the x and y visual coordinate axes at each viewing position are determined using the measured positions of the video images of the point and the data from the optical calibration. The method for doing this was fully disclosed in the referenced co-pending application. Then, two vectors, called i'visual location t'vectors, are formed from these tangents, and are expressed as column matrices. These vectors are defined as:

$$\overline{a}_{v1} = \begin{bmatrix} \tan(\alpha_{x1}) \\ \tan(\alpha_{y1}) \\ 1 \end{bmatrix} \text{ and } \overline{a}_{v2} = \begin{bmatrix} \tan(\alpha_{x2}) \\ \tan(\alpha_{y2}) \\ 1 \end{bmatrix} \quad (1)$$

where, for instance, ($\alpha_{x1}$, $\alpha_{y1}$) are the angular positions for the point of interest that were determined at P1.

If $\overline{d}$ is known in the visual coordinate system, and is also written as a column matrix, then the three dimensional spatial position of the point of interest can be calculated using the following matrix equation:

$$\vec{r}_m = \begin{bmatrix} x \\ y \\ z \end{bmatrix} = \frac{1}{2}[\overline{a}_{v1} \ \overline{a}_{v2}][a_{v1} \ -a_{v2}]^{LI} \vec{d}_v \quad (2)$$

where the subscript "v" on d indicates that here the perspective displacement is expressed in the same coordinate system as are the visual location vectors. In Equation (2) the position of the point is expressed in that coordinate system parallel to the visual coordinate system which has its origin midway between P1 and P2.

Equation (2) uses the concept of the left pseudo-inverse of a matrix. The left pseudo-inverse of a matrix D can be calculated as:

$$D^{LI}=(D^T D)^{-1} D^T \quad (3)$$

where $D^T$ is the transpose of matrix D and the superscript (−1) denotes the conventional matrix inverse.

Once the coordinates of a number of points of interest are known in a single coordinate system, distances between these points are easy to calculate using the Pythagorean Theorem.

One problem with this system, when used with a standard borescope as shown in FIG. 1, is depicted in FIG. 6. Here, the lens tube of the borescope is not perfectly straight. Thus, when the borescope is clamped to the BPA at different points along its length, the geometrical relationship between the perspective displacement $\vec{d}$ and the visual coordinate system changes. This means that, for accurate work, an alignment calibration must be performed whenever the borescope is clamped at different positions along its length.

Figure 7A:
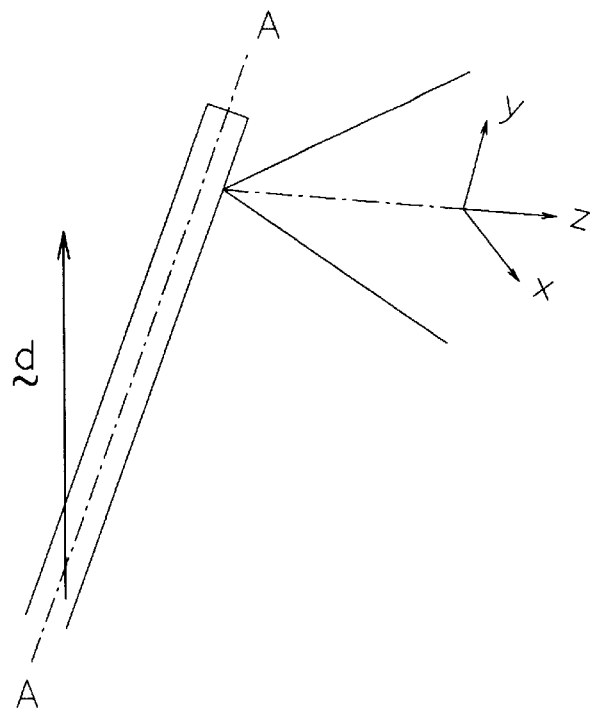
FIGS. 7A, 7B depict the change in alignment between the perspective displacement and the visual coordinate system that can occur if the borescope is rotated about an axis that is not parallel to the perspective displacement.
Figure 7B:
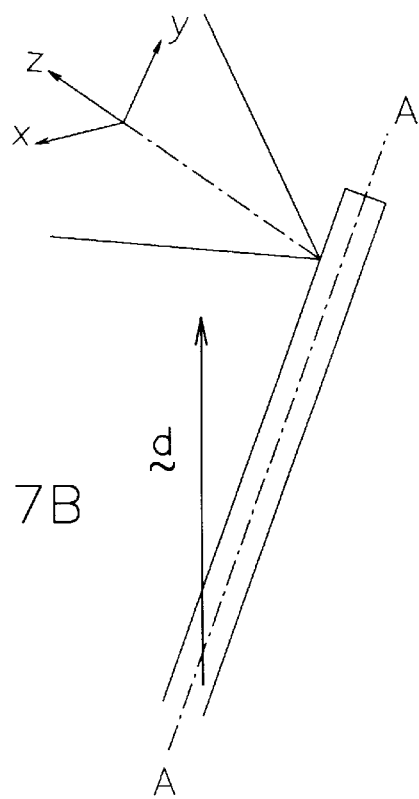

A second problem is depicted in FIGS. 7A and 7B. Coordinate axes parallel to the visual coordinate system are drawn in FIG. 7 to make it easier to visualize the geometrical relationships. In these Figures the borescope is shown aligned along a mechanical axis (A—A). The Figure is drawn in the plane which contains the mechanical axis and which is also parallel to the perspective displacement $\vec{d}$.

In FIG. 7B the borescope has been rotated by 180 degrees about the mechanical axis with respect to its position in FIG. 7A. In FIG. 7A, the component of the visual x axis that is perpendicular to the page is directed into the page. In FIG. 7B, the component of the visual x axis that is perpendicular to the page is directed out of the page.

The orientation of $\vec{d}$ with respect to the visual coordinate system is not the same in FIGS. 7A and 7B. (This may be most clear when considering the visual z axis.) Thus, when the axis of mechanical rotation of the borescope is not parallel to the perspective displacement, the orientation of the perspective displacement in the visual coordinate system will change when the borescope is rotated about that mechanical axis. For the system shown in FIG. 1, the mechanical axis of rotation is determined by the V groove of lower V block 142 of the BPA. This means that an alignment calibration must be performed whenever the borescope is clamped at a new angular orientation with respect to the BPA, unless the V groove is accurately aligned along the translation axis of the translation stage.

A third problem is caused by the characteristics of the lens tube of a standard borescope. The envelope of the lens tube is typically made of thin wall stainless steel tubing. Such an envelope is unlikely to be perfectly circular at any position along its length, and it has already been discussed how unlikely it is to be straight. Rotation of such a geometrically imperfect envelope in a V groove will lead to a varying orientation of $\vec{d}$ with respect to visual coordinates even if the V groove were aligned with d and the clamping position along the length tube were unchanged. Once again, the situation is that if the borescope is moved with respect to the BPA, then alignment calibration must be repeated, at least for accurate work.

One approach to addressing these problems would be to characterize the alignment of the perspective displacement with respect to the visual coordinate system as a function of the position and orientation of the borescope with respect to the BPA. While this would work in theory, the amount of calibration effort necessary and the likelihood of poor repeatability of borescope orientation, due to the characteristics of the lens tube envelope, make this approach impractical.

B. Description of a First Embodiment

Figure 8:
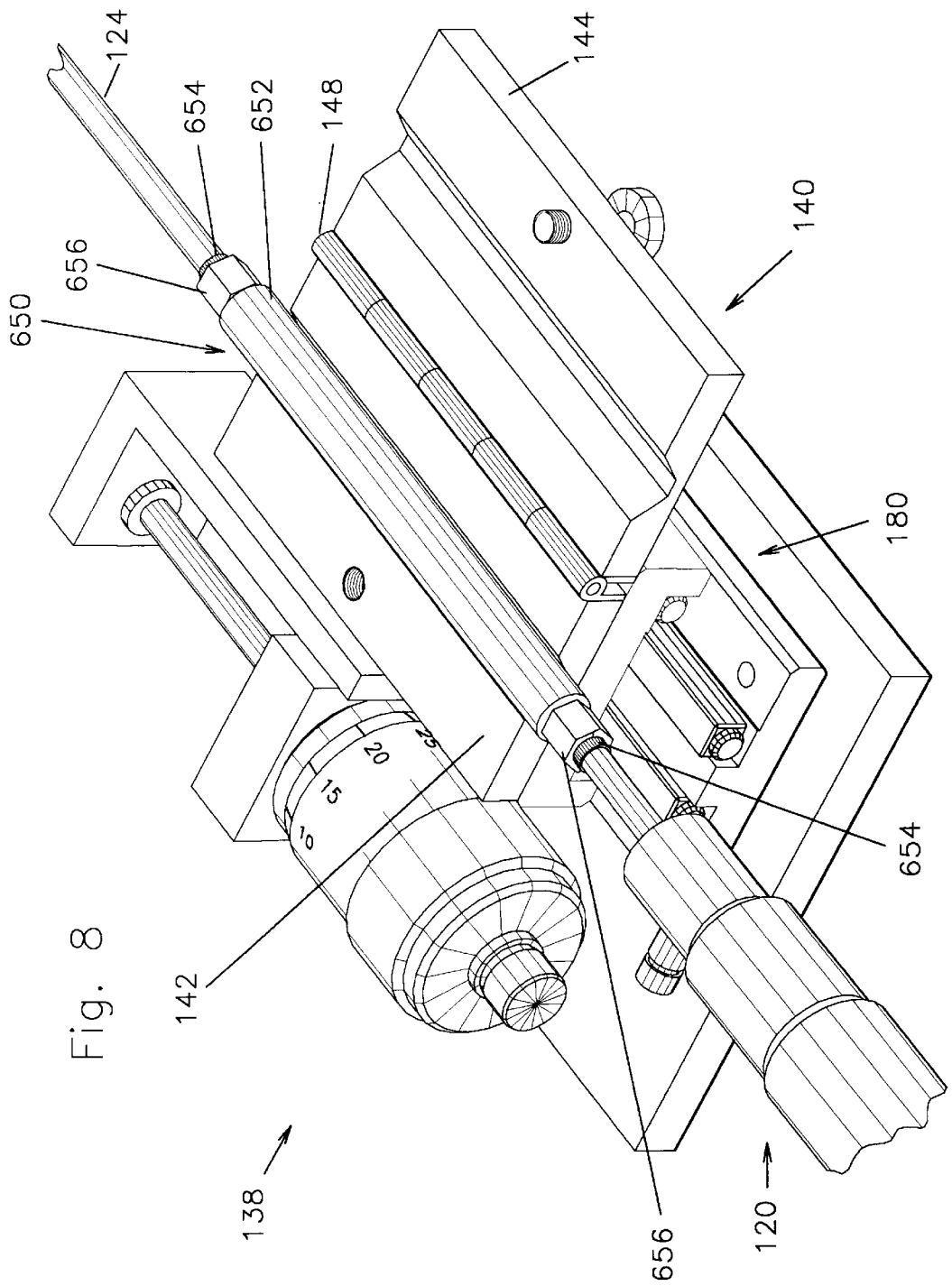
FIGS. 8A, 8B are a perspective view of a first embodiment of the present invention.

FIG. 8 shows a first embodiment of a system which solves these problems. Since this is a modification of the system shown in FIG. 1, the same reference numerals are used to refer to elements for which the function is unchanged. In FIG. 8, clamp 140 is shown in the open position in order to better show the modifications.

A portion of borescope lens tube 124 has been enclosed by a metrology sleeve or calibration sleeve 650. Calibration sleeve 650 is comprised of a thick-walled cylindrical tube 652 with sleeve ferrules 654 attached at either end. Sleeve nuts 656 screw on to ferrules 654 to clamp the assembly to lens tube 124 at any selected position along lens tube 124.

The outer diameter of cylindrical tube 652 is fabricated to be accurately circular and straight. This is typically done by a process known as centerless grinding. Tube 652 is preferably made of a rather hard material, for instance high carbon steel coated with hard chrome, or case-hardened stainless steel. On the other hand, upper V block 144 is preferably made of a somewhat softer material, for instance, low carbon steel, aluminum, or brass. Because of these relative hardnesses, and because of the thick wall of tube 652, it is no longer necessary to use a layer of resilient material to line upper V block 144, and thus it is not shown in FIG. 8. This also means that a much higher clamping pressure can be used in this system than could be used in the original system of FIG. 1.

Calibration sleeve 650 lies in the V groove in lower V block 142. The dimensions of the V grooves in both lower V block 142 and upper V block 144 have been modified from those shown in previous figures in order to clamp the larger diameter of tube 652. In order for the groove in lower V block 142 to act as the position reference for sleeve 650, and hence, ultimately, for video borescope 120, hinge 148 is now fabricated with an appropriate amount of play, so that the groove in upper V block 144 takes a position and orientation which is determined by sleeve 650 when clamp 140 is closed.

The groove in lower V block 142 is accurately aligned to the translation axis of stage 180 to a predetermined tolerance using one of the methods to be described later.

Figure 8A:
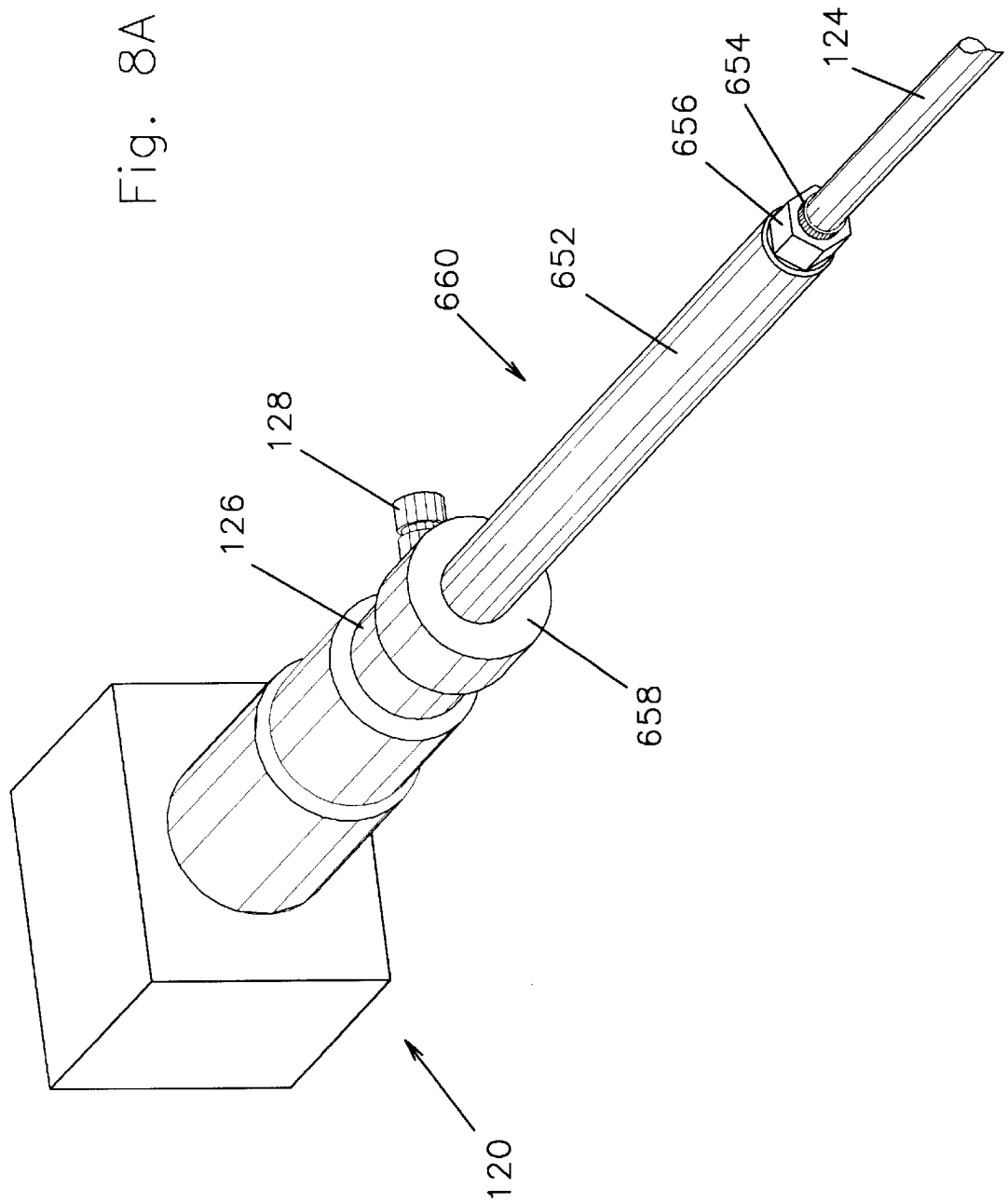

An alternative embodiment of a calibration sleeve is shown in FIG. 8A. There a strain-relieving calibration sleeve 660 is shown attached to video borescope 120. At the distal end, sleeve 660 is attached to borescope lens tube 124 with the same ferrule (654) and nut (656) system that was shown in FIG. 8. At the proximal end, sleeve 660 is attached to the body of the endoscope through a torque transferring clamping collar 658. In the embodiment that was shown in FIG. 8, the overhanging torque due to the proximal (rear) portion of borescope 120 is concentrated on the small diameter lens tube 124 at the point at which lens tube 124 exits ferrule 654. Video endoscope systems vary in the size and weight of their proximal portions, and it is probable that in some cases, the overhanging torque will exceed the capacity of lens tube 124 to resist bending. In this alternative embodiment, collar 658 transfers this torque to a more robust portion of the endoscope. As shown in FIG. 8A, with the generic video borescope 120, collar 658 is securely clamped to illumination adapter 126; this clamping can be done with any of several common and well-known techniques. Collar 658 is constructed so as to provide the necessary operating clearance for fiber optic connector 128. Depending on the design of the borescope being used, it may be that some other portion of the borescope will be the most suitable attachment point for collar 658.

C. Operation of the First Embodiment

Consider FIG. 8 once again. In use, calibration sleeve 650 is semi-permanently attached to borescope 120. When nuts 656 are tightened, sleeve ferrules 654 grab tightly without marring or denting the surface of lens tube 124, fixing the relative locations of lens tube 124 and the outer cylindrical surface of sleeve 650. Since the visual coordinate system is fixed with respect to the outer envelope of the borescope, the outer surface of sleeve 650 is fixed with respect the visual coordinate system. I call the assembly of borescope 120 and calibration sleeve 650 the perspective measurement assembly.

The perspective measurement assembly can be located at any position inside clamp 140, and can be clamped in that position, as long as a significant length of sleeve 650 is contained within the clamp. The action of placing sleeve 650 in the V groove in lower V block 142 constrains four degrees of freedom of the motion of sleeve 650. The two unconstrained motions are rotation about the axis of the sleeve, and translation along that axis. Translation is, of course, limited to a range of distances over which a significant length of the sleeve will be contained inside the clamp. Since the borescope is clamped inside the sleeve, its motion is similarly constrained and controlled, as is the motion of the visual coordinate system. These two degrees of freedom are precisely those necessary to allow borescope 120 to view objects at different positions with respect to BPA 138 (FIG. 1).

Since the groove in lower V block 142 is accurately aligned with the translation axis of stage 180, and since the outer surface of sleeve 650 is accurately cylindrical, the relative orientations of $\vec{d}$ and the visual coordinate system do not change as the perspective measurement assembly is rotated or translated in lower V block 142. Note that there need be no particular orientation of the visual coordinate system with respect to the axis of the cylindrical outer surface of sleeve 650. The only requirements for there to be a constant relative orientation between $\vec{d}$ and the visual coordinate system are that the surface of sleeve 650 be accurately cylindrical, and that the axis of the locating V groove be accurately directed along $\vec{d}$.

For making measurements on objects at widely differing depths inside enclosure 110 (FIG. 1), sleeve 650 can be moved on lens tube 124, but when it is moved, a new alignment calibration will be required, in general. The range of depths that can be accommodated by a perspective measurement assembly without recalibration is determined by the length of sleeve 650. For many users a limited range of available measurement depths is not a problem because their objects of interest are confined to a small range of depths inside the enclosure.

Calibration sleeve 650 could be made nearly as long as lens tube 124. This suggests another option for eliminating the need for routine alignment calibrations. I call this option the metrology borescope. A metrology borescope, a new instrument, is a rigid borescope built with a lens tube which is thicker, stiffer, and harder than normal. The outer envelope of lens tube 124 of a metrology borescope is precision fabricated to be accurately cylindrical. Such a scope does not need calibration sleeve 650 in order to provide accurate perspective dimensional measurements with only a single alignment calibration.

Standard borescopes, with their thin envelopes, tend to get bent in use. A small bend does not ruin a borescope for visual inspection, but it would ruin the accuracy of any calibrated perspective measurement assembly. Since the metrology borescope is more resistant to such bending, it is the superior technical solution.

An additional advantage of the system shown in FIG. 8 over that shown in FIG. 1 is that borescopes with different lens tube diameters can be fitted with appropriate calibration sleeves of the same outer diameter. Thus, when the calibration sleeve is placed into lower V block 142, the centerline of the borescope is always at the same position with respect to the BPA, which is not the case when different diameter borescopes are directly inserted into the V block. Keeping this centerline at a constant position makes the mounting of the BPA with respect to enclosure 110 and inspection port 112 (FIG. 1) less complicated when borescopes of different diameters are to be accommodated.

I have already stated that the V groove in lower V block 142 is accurately aligned with the translation axis of translation stage 180. I now explain exactly what this means, and then how that condition can be achieved.

A V groove is made up of two bearing surfaces which, ideally, are sections of flat planes. If these surfaces are perfect, then the corresponding planes will intersect in a straight line. It is when this line of intersection is parallel to the translation axis of stage 180, that it can be said that the V groove is accurately aligned with the translation.

The purpose of the V groove is to locate the cylindrical outside diameter of the calibration sleeve accurately and repeatably. By locating a cylindrical object accurately, I mean that for a short section of a perfect cylinder, the orientation of the axis of the cylindrical section does not depend on where along the length of the V groove the cylindrical section happens to bear, and that there is a continuous single line contact between each bearing surface and the cylindrical section, no matter where that section happens to lie along the V groove, and no matter how long that section is.

A V groove will serve to locate a cylindrical object accurately even if the bearing surfaces are not planar, just so long as three conditions hold. First, each of the bearing surfaces must either have a symmetry about a straight line axis or must be perfectly planar. Second, the straight line axis of one surface must be parallel to the axis or plane of the other surface. Third, surfaces with symmetry about a straight line axis must either be convex or have a sufficiently large radius of curvature that there is only one line of contact between the cylindrical object and the surface.

This means, for instance, that two accurately cylindrical bodies can serve to accurately locate a third cylinder just as long as the axes of the first two cylinders are parallel, and such a system could be used instead of the preferred V groove.

It is also possible to form two physical lines of contact, by cutting a cylindrical groove into a plane surface or into a larger radius cylindrical groove, for example. These physical lines can serve to accurately locate a cylinder, but only if the cylindrical groove is oriented accurately parallel to the plane surface or cylinder into which it is cut. If the cylindrical groove is not so oriented, the contact lines formed thereby will not be straight and will not serve to accurately locate a cylindrical body.

In order to locate the calibration sleeve repeatably, it is necessary to pay appropriate attention to maintaining the cleanliness of both the outer surface of the calibration sleeve and of the locating surface on the BPA, whether that surface is embodied as a V groove or as some other appropriate geometry.

To maintain the accuracy of the perspective measurement, one must maintain the orientation of the visual coordinate system with respect to the outer surface of the calibration sleeve, and one must also maintain the alignment of the BPA reference surface with respect to the perspective displacement. In order to maintain these geometrical relationships over a wide range of operating temperatures, one must pay careful attention to the effects of differential thermal expansion, especially in those embodiments which use an alignable BPA reference surface.

D. How to Achieve Accurate Alignment of the BPA Reference Surface

In any discussion of "accuracy" must include a definition of the size of errors which are allowed while still justifying the label "accurate". In my perspective measurement system, the error of interest is the error in the dimensional measurement being made. As far as the alignment of the system is concerned, an unknown error in the orientation of $\vec{d}$ with respect to the visual coordinate system will cause a systematic error in the distance measurement.

Analysis shows that a misalignment of $\vec{d}$ will cause a systematic measurement error which will vary linearly with the distance (range) between the object being measured and the nodal point of the borescope optical system. That is, this systematic error in a distance measurement can be expressed as a fraction of the range of the object, for example, 1 part in 1000, or as an error angle, e.g. 1 milliradian. In detail, the error in any given measurement depends on the position of the object in the apparent field of view of the borescope in each of the two views, and on the fractional portion of the field of view subtended by the distance being measured.

In the worst case, the error in the measured distance is approximately equal to the angular error in the orientation of $\vec{d}$ times the range to the object. That is, a 1 milliradian angular error in the orientation of $\vec{d}$ corresponds approximately to a worst case distance measurement error of 1 part in 1000 of the range.

A given level of acceptable systematic measurement error will correspond to an acceptable level of misalignment. For the purposes of this discussion, I will define two levels of acceptable error. I call a "Class 1" measurement one that is accurate to 1 part in 1000 of the range. I call a "Class 2" measurement one that is accurate to 1 part in 10,000 of the range. These acceptable error levels are consistent with the random error capabilities of the perspective measurement system when it is implemented with standard endoscopy equipment. A random error of 1 part in 1000 of the range is fairly straightforward to achieve using a standard video borescope, while achieving 1 part in 10,000 random error requires either (1) the use of a high resolution borescope optical system and a high resolution video camera back and some averaging of measurements, or (2) the averaging of a large number of measurements.

The achievement of a misalignment of 1 millirad, i.e., 0.001 inch per inch, is straightforward by use of precision machining techniques, as long as translation stage 180 has been fabricated with accurate mechanical references to its translation axis. If it has not been so fabricated, one proceeds as follows.

Usually, the top surface of moving table 184 of stage 180 (FIG. 2) is guaranteed by the manufacturer to be parallel to the translation to within a specified tolerance. Often, this tolerance is 0.0001 inch per inch. If the top of the moving table has not been accurately aligned with the translation, then one can measure the pitch of the top surface by suspending a dial indicator above the stage and indicating on the top surface of moving table 184 as it translates below. This known pitch can then be compensated for in the machining of lower V block 142.

If there is not a convenient reference for the direction of the translation axis as measured in the plane of the top surface of moving table 184, suitable reference holes are easily made by mounting the stage on a drilling machine and using the motion of the stage itself to determine the relative positions of the holes.

Once stage 180 has been characterized and/or modified, lower V block 142 is fabricated with standard machining techniques while paying particular attention to two key factors. First, the bottom surface of lower V block 142 must be oriented accurately parallel to the translation axis of the fabrication machine when the V groove is cut into its upper surface (or tilted to offset the pitch of the top of moving table 184, measured as discussed above). Secondly, the V groove, and any reference holes, are machined with a fixed tool spindle location and with the machine tool moving lower V block 142 only along a single translation axis. This guarantees that the V groove will be parallel to the line between the centers of the reference holes to an accuracy determined by the straightness of the machine tool translation axis.

The achievement of a misalignment appropriate to Class 2 measurements, i.e. 100 microradians, by precision machining is possible, but difficult and expensive. One way to make it more feasible is to do the final grinding of the V groove into block 142 with block 142 mounted to the translation stage. The stage motion itself is used to provide the necessary motion of the block with respect to the grinding wheel. The disadvantage of this approach is that the length of the V groove is limited to somewhat less than the length of travel of the stage. The advantage is that the alignment of the V groove with the translation will be accurate to within the accuracy of translation of the stage.

For Class 2 accuracy, it may be preferable to align the V with respect to the translation of the stage. One way to accomplish this alignment is to use shims to adjust the position of lower block 142 in pitch with respect to the top of moving table 184 and in yaw with respect to a reference surface attached to the table top. A second way is to split lower block 142 into two plates with a variable relative alignment in pitch and yaw. Such a device would be similar to and work on the same principles as the Model 36 Multi-axis Tilt Platform sold by the Newport Corporation of Irvine, Calif. The upper plate of this assembly is steered with respect to the lower plate in pitch and yaw through the use of adjusting screws, while the lower plate is conventionally attached to the top of moving table 184.

Figure 9:
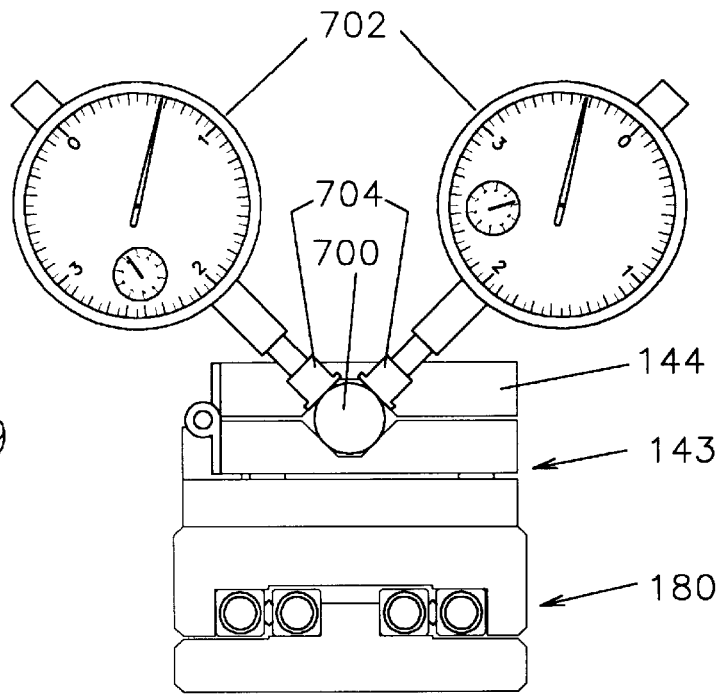
FIG. 9 is an end elevation view of a test rig for determining the alignment of a V groove with respect to the translation axis of a translation stage.

A rig for determining the alignment of the V groove to the translation of the stage is depicted in FIG. 9. Here is shown a front elevation view of a translation stage 180, to which is attached a split lower V block 143. Split lower V block 143 is constructed as discussed in the previous paragraph. As before, upper V block 144 acts as a clamp; the screw or mechanism which provides clamping force is not shown. A reference cylinder 700 is clamped into split lower V block 143 so that a suitable length of cylinder 700 extends out of the clamp towards the observer. Reference cylinder 700 is selected to be straight and circular to a very high degree of accuracy. A pair of dial indicators 702 are mounted to the work surface by conventional means which are not shown. Indicators 702 are suspended over reference cylinder 700 and disposed to either side of it. Sensing feet 704 of dial indicators 702 contact the shaft at the same distance from the clamp as measured along cylinder 700. Sensing feet 704 have a flat surface over most of their diameter in order to avoid errors due to the imperfect alignment of the indicator measurement axis with the axis of reference cylinder 700.

To determine the desired alignment, stage 180 is translated back and forth along its length of travel, and the readings of the dial indicators are monitored. Errors in pitch of the V groove are indicated by changes in the average of the two dial indicator readings. Errors in yaw are indicated by changes in the difference of the two readings. The alignment of the V groove is perfect when the dial indicators do not change as the stage is translated.

The arrangement of dial indicators 702 is not restricted to that shown in FIG. 9. One could orient one of the indicators so that it was suspended vertically above reference cylinder 700, and the other could be oriented horizontally. Then one indicator would directly indicate pitch, while the other would directly indicate yaw. The only requirement is that the two indicators not be oriented in exactly the same direction, and for best sensitivity and most convenience, there should be a right angle between their orientations.

One can check for the presence of geometrical imperfections in the combination of reference cylinder 700 and the V groove in lower V block 143 by loosening the clamp, rotating reference cylinder 700 about its axis to another angular position, tightening the clamp, and redoing the check. One can also repeat the test at different positions along the length of cylinder 700 to check for errors in its straightness. A good reference for the theory and practice of making such measurements is Handbook of Dimensional Measurement, 2nd Edition, by Francis T. Farago, Industrial Press, New York, 1982.

One could directly indicate on the plane surfaces of the V groove rather than using a reference cylinder as I have shown. But in that case, one would be measuring imperfections in these surfaces as well as their alignment, when what one really cares about is how the existing V groove acts to locate a cylinder. Since accurate reference cylinders are readily available, I prefer the method I have shown.

Of course, it must be kept in mind that one cannot expect to determine errors in the geometry of cylinder 700 or in the V groove in lower V block 143 to a level better than that provided by the straightness and repeatability of motion of translation stage 180. Since the purpose of this test rig is to align the V groove with respect to this motion, errors in this motion do not affect the validity of the results.

Figure 10:
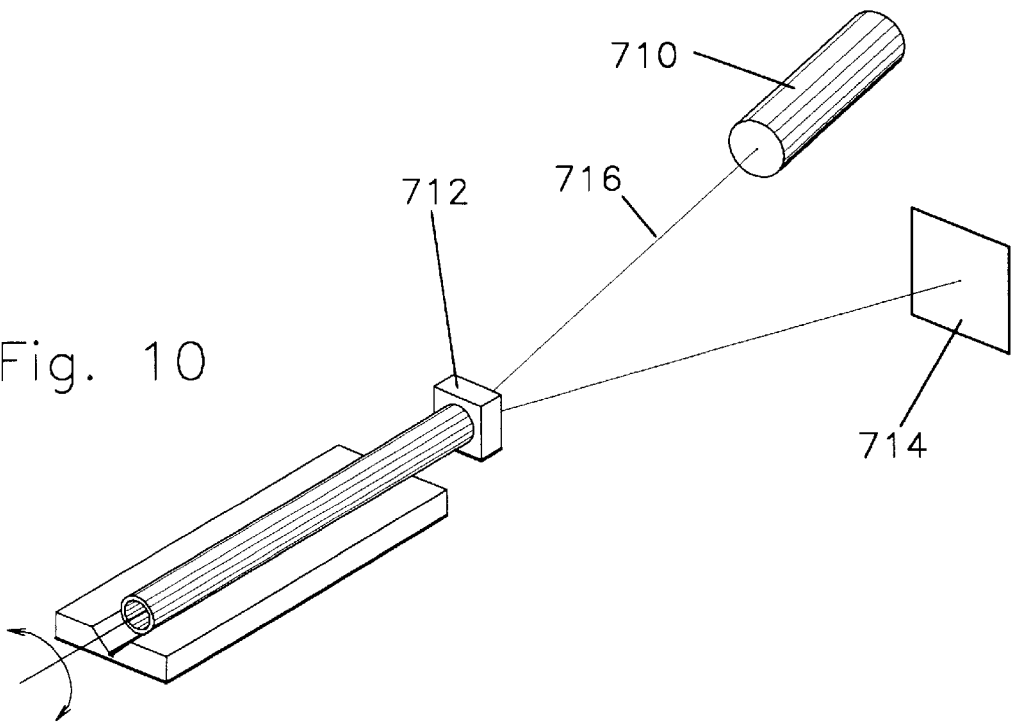
FIG. 10 depicts the process of determining the alignment errors caused by imperfections in the geometry when a cylinder rotates in a V groove.

One can check for the integrity of the rotation of a cylinder in a V block by mounting a mirror on an adjustable mirror mount so that the mirror is approximately perpendicular to and centered on the axis of the cylinder. This process is depicted in FIG. 10. In FIG. 10 a laser 710 produces a laser beam 716. Laser beam 716 is reflected from a mirror which is part of mirror mount assembly 712. The beam reflected from the mirror is allowed to impact a viewing screen 714.

The mirror mount is adjusted to produce the smallest motion of the laser spot as the cylinder is rotated in the V block. Any residual motion of the spot, which cannot be reduced by adjustment of the angular orientation of the mirror, is due to non-constant angular orientation of the cylinder as it rotates while maintaining contact with the V block. The variation of the orientation of the axis of the cylinder can be sensed to within a few tenths of a milliradian in this way. A sensitivity on the order of a microradian can be achieved, once the mirror has been aligned as shown here, by viewing the mirror with an autocollimator which has been aligned nearly perpendicular to the mirror, and again rotating the cylinder.

It is possible to conceive of a motion of the cylinder in the V block that is not perfect, but is such that the mirror remains at a constant angular orientation while the cylinder is being rotated. (One way is for the cylinder to wobble as it rotates.) What is important about such a situation is that any motion which causes an error in the perspective measurement will also cause an error when being tested by the technique depicted in FIG. 10.

E. Description of a Second Embodiment

Figure 11:
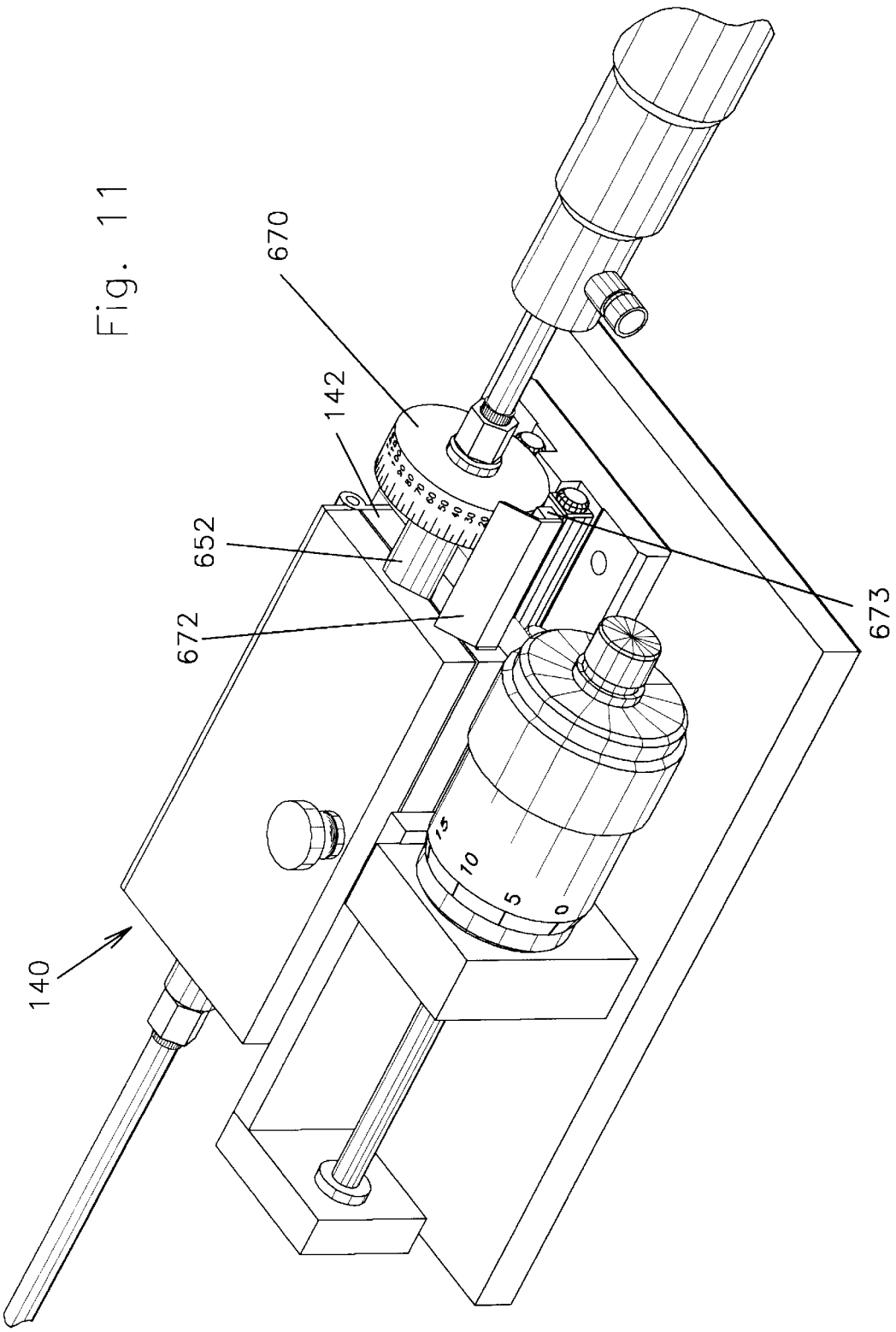
FIG. 11 is a perspective view of the mechanical portion of a second embodiment of the present invention.

The mechanical portion of a second embodiment of my improved system is shown in FIG. 11. This differs from the first embodiment in that there is now an angle scale or protractor 670 attached to cylindrical tube 652. A protractor pointer 672 is attached to a pointer mounting bar 673 which is in turn attached to lower V block 142. Pointer 672 has sufficient length to enable the angular orientation of the perspective measurement assembly to be determined no matter where it is located in its range of translation with respect to clamp 140.

In this embodiment, the V groove in lower block 142 need not be accurately aligned with the perspective displacement.

Another option would be to use the strain-relieving calibration sleeve 660 as depicted in FIG. 8A. Then an angular scale could be advantageously marked on the outer diameter of collar 658.

F. Operation of the Second Embodiment

It was shown in FIG. 7 that the alignment of the perspective displacement, $\vec{d}$, in the visual coordinate system is a function of the rotation of the perspective measurement assembly about the axis of the cylindrical surface of the calibration sleeve. In this second embodiment, the acquisition of an additional piece of information during the measurement, and an additional step in alignment calibration, enable one to calculate the alignment of $\vec{d}$, and thus make an accurate perspective measurement, despite the presence of a misalignment between the axis of the calibration sleeve and the perspective displacement. I will explain the operation of the measurement in this section, and the necessary additional calibration of the system in the next section.

Figure 12A:
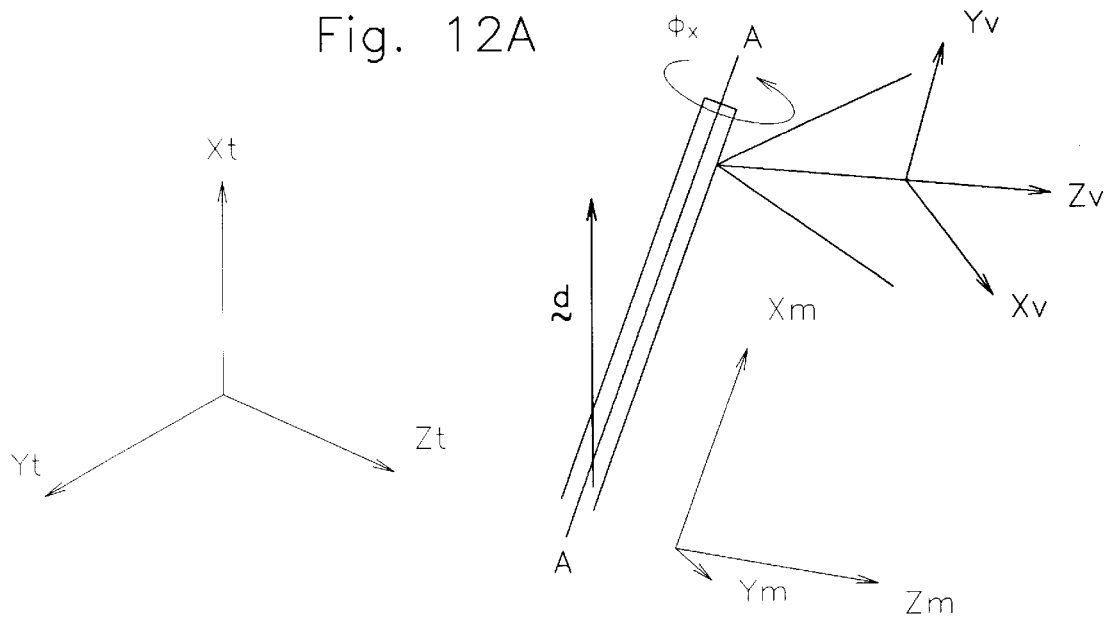
FIGS. 12A, 12B depicts the relationships between the three Cartesian coordinate systems used in analyzing the effects of a misalignment of the borescope axis of rotation with respect to the perspective displacement.
Figure 12B:
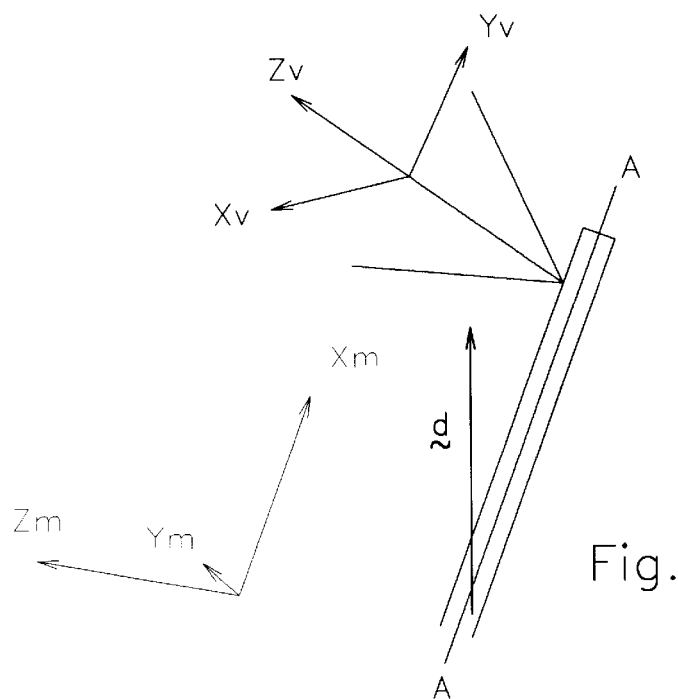

FIG. 12 is similar to FIG. 7 but it contains additional information. As before, a visual coordinate system $(x_v, y_v, z_v)$ is defined by the x and y axes of the video camera focal plane, and the optical axis of the borescope. In FIG. 12 coordinate axes parallel to the visual coordinate system are shown in the field of view of the borescope. As before, the Figure is drawn in the plane which contains the axis of mechanical borescope rotation, A—A, and which is parallel to the perspective displacement, $\vec{d}$. None of the visual coordinate axes $x_v, y_v, z_v$ are necessarily contained in the plane of the Figure. Again as before, in FIG. 12A, the component of the visual x axis that is perpendicular to the page should be visualized as being directed into the page, while it should be visualized as being directed out of the page in FIG. 12B.

One may define a borescope mechanical coordinate system which rotates with the borescope, which has a fixed relationship with respect to the visual coordinate system, and which has its x axis parallel to A—A as follows:

(1.) The $x_m$ axis is oriented along A—A.

(2.) The $y_m$ direction is chosen to be perpendicular to both the optical axis, $z_v$, and to $x_m$. This can be expressed mathematically as:

$$\hat{y}_m = \frac{\hat{z}_v \times \hat{x}_m}{|\hat{z}_v \times \hat{x}_m|} \quad (4)$$

where the hat indicates a unit vector and x indicates the vector cross product.

(3.) Finally, the $z_m$ axis is chosen to be perpendicular to both $x_m$ and $y_m$ axes in the usual way as:

$$\hat{z}_m = \frac{\hat{x}_m \times \hat{y}_m}{|\hat{x}_m \times \hat{y}_m|} \quad (5)$$

The mechanical coordinate system $(x_m, y_m, z_m)$ is depicted in FIG. 12. One important implication of this definition is that the optical axis. $z_v$, is guaranteed to lie in the $(z_m, x_m)$ plane.

Also shown in FIG. 12 is a translation coordinate system, $(x_t, y_t, z_t)$, which has a fixed orientation with respect to the translation stage. The $x_t$ axis is defined to lie along the perspective displacement. $\vec{d}$. For the moment, the directions of the $y_t$ and $z_t$ axes are taken to be arbitrary, but the $(x_t, y_t, z_t)$ system is defined to be a conventional right-handed Cartesian coordinate system.

For the purposes of this discussion, all of these coordinate systems will be assumed to have origins at the same point in space, although they are drawn separated in FIG. 12 for clarity.

What one needs is an expression for $\vec{d}$ in the visual coordinate system. This expression will depend on the rotation of the borescope about the mechanical axis A—A. The parameter for this rotation is taken to be the angle $\phi_x$.

The transformation of the coordinates of a vector when a coordinate system is rotated is exactly the same as the transformation of the axes of the coordinate system. In general, to align one three-dimensional coordinate system with another, rotations about three axes will be required. It is a fact that there is no unique way to describe the rotations necessary to align one 3D coordinate system with another. No matter how the sub-rotations are defined, the result of a series of sub-rotations depend on the order in which the sub-rotations are performed. Thus, in order to discuss rotations in three dimensions, one must carefully define what procedure is being used for a series of sub-rotations.

I define the specific procedure for rotating the mechanical coordinate system to align it with the translation coordinate system as follows:

(a.) Rotate the m coordinate system about $x_m$ until $y_m$ lies in the $(x_t, y_t)$ plane.

(b.) Rotate the m coordinate system about $y_m$ until $z_m$ coincides with $z_t$.

(c.) Rotate the m coordinate system about $z_m$ until $x_m$ coincides with $x_t$ (and $y_m$ coincides with $y_t$).

Mathematically, this procedure can be expressed as:

$$\vec{v}_t = R_z(\phi_z) R_y(\phi_y) R_x(\phi_x) \vec{v}_m = R v_m \quad (6)$$

In Equation (6), $v_t$ and $v_m$ are 3×1 matrices which contain the components of any arbitrary vector as expressed in the translation and mechanical coordinate systems respectively. The angles $\phi_x$, $\phi_y$, and $\phi_z$ are the angles by which the coordinate system is rotated in each step of the procedure. At each step, the angle is measured in the coordinate system that is being rotated. The positive direction of rotation is defined by the right hand rule. The 3×3 rotation matrices $R_x$, $R_y$, and $R_z$, which are each defined in a standard way, describe the effects of each individual sub-rotation. Composite rotation matrix R is simply the product of the three component rotation matrices.

The standard definitions of the component rotation matrices are:

$$R_z(\theta_z) = \begin{bmatrix} \cos\theta_z & \sin\theta_z & 0 \\ -\sin\theta_z & \cos\theta_z & 0 \\ 0 & 0 & 1 \end{bmatrix} \quad (7)$$

$$R_y(\theta_y) = \begin{bmatrix} \cos\theta_y & 0 & -\sin\theta_y \\ 0 & 1 & 0 \\ \sin\theta_y & 0 & \cos\theta_y \end{bmatrix}$$

-continued $$R_x(\theta_x) = \begin{bmatrix} 1 & 0 & 0 \\ 0 & \cos\theta_x & \sin\theta_x \\ 0 & -\sin\theta_x & \cos\theta_x \end{bmatrix}$$

Step (a.) of the procedure implicitly states that $\phi_x=0$ when $y_m$ lies in the $(x_t, y_t)$ plane. In the embodiment shown in FIG. 11, the orientation of the perspective measurement assembly for which $\phi_x=0$ is defined by the scale on protractor 670. Together, these two facts mean that it is the location of the zero point on the scale of protractor 670 which defines the orientation of the $y_t$ and $z_t$ axes. The orientation of these axes can no longer be considered arbitrary.

The inverse transformation to Equation (6), that is, the procedure for rotating the translation coordinate system to align it with the mechanical system, can be expressed as:

$$\vec{v}_m = R_x(-\phi_x)R_y(-\phi_y)R_z(-\phi_z)\vec{v}_t = R_x^{-1}(\phi_x)R_y^{-1}(\phi_y)R_z^{-1}(\phi_z)\vec{v}_t \quad (8)$$

Figure 13:
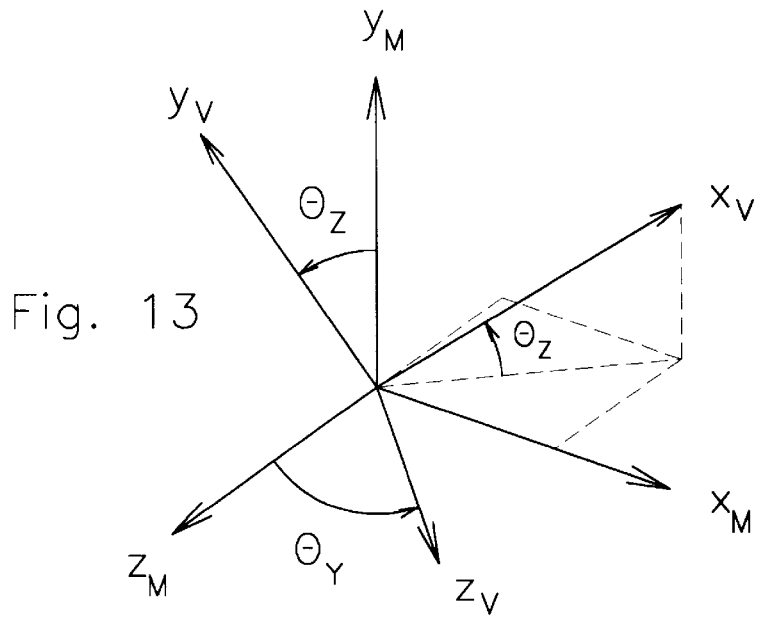
FIG. 13 shows the relationship of the borescope visual and mechanical coordinate systems.

Recall that the mechanical coordinate system was defined so that the visual z axis is confined to the mechanical (x, z) plane. The relationship of the visual and mechanical coordinate systems is depicted in FIG. 13. Because of the way the relationship between these two coordinate systems was defined, there are only two rotation angles necessary to align one with the other. The specific procedure for rotating the mechanical coordinate system so that it is aligned with the visual coordinate system is simply:

(a.) Rotate about the mechanical y axis by angle $\theta_y$.
(b.) Rotate about the mechanical z axis by angle $\theta_z$.

In mathematical terms this is:

$$\vec{r}_v = R_z(\theta_z)R_y(\theta_y)\vec{r}_m \quad (9)$$

Angle $\theta_y$ represents a rotation of the optical axis with respect to the mechanical z axis; this rotation is confined to the mechanical (x, z) plane. Angle $\theta_z$ represents a rotation of the visual coordinate system about the optical axis.

Combining Equations (8) and (9), one can express the relationship between a vector as expressed in the translation and visual coordinate systems as:

$$\vec{r}_v = R_x(\theta_z)R_y(\theta_y)R_x^{-1}(\phi_x)R_y^{-1}(\phi_y)R_z^{-1}(\phi_z)\vec{r}_t \quad (10)$$

Since the displacement vector, as expressed in translation coordinates is simply $$\vec{d} = d\begin{bmatrix} 1 \\ 0 \\ 0 \end{bmatrix},$$

one has:

$$\vec{d}_v = R_z(\theta_z)R_y(\theta_y)R_x^{-1}(\phi_x)R_y^{-1}(\phi_y)R_z^{-1}(\phi_z)\begin{bmatrix} d \\ 0 \\ 0 \end{bmatrix} \quad (11)$$

Therefore, to determine the three-dimensional position of a point of interest in this second embodiment, one determines the visual location vectors $\vec{a}_{v1}$ and $\vec{a}_{v2}$ as usual. One also records the reading of protractor 670 as indicated by pointer 672. This is the angle $\phi_x$. One then uses the four angles ($\theta_z$, $\theta_y$, $\phi_y$, $\phi_z$) as determined in an alignment calibration, in Equation (11) to determine the displacement vector as expressed in visual coordinates. This alignment calibration is discussed below. Finally, one uses Equation (2) to determine the position of the point.

There are many other ways that the rotation of the perspective measurement assembly with respect to the BPA could be determined. For instance, the rotation could be sensed with an optical or an electrical transducer, and the user would then avoid having to read a scale manually. It is also possible to attach the protractor to the BPA and the pointer to the perspective measurement assembly to achieve the same result as does the preferred embodiment shown in FIG. 11. In addition, the angle scale could be read more precisely when necessary by using a conventional vernier scale index instead of the simple pointer 672.

It is important to consider how accurately one must determine $\phi_x$ in order to achieve the accuracy desired in the perspective measurement. Assume that the misalignment of the mechanical x axis with respect to the translation x axis is small enough that the sines of the angles $\phi_y$ and $\phi_z$ can be replaced with the angles themselves. Then it can be calculated, by differentiation of Equation (11), that the worst case error component in $\vec{d}_v/d$ is $\sqrt{\phi_y^2 + \phi_z^2}$ times the error in $\phi_x$. If we take $\phi_y$ and $\phi_z$ to have equal magnitudes, and call that magnitude $\phi_\perp$, then the worst case error component in $\vec{d}_v$ is $\sqrt{2}\phi_\perp\Delta_{\phi x}$. Thus, any combination of misalignment, $\phi_{195}$, and rotational measurement error, $\Delta_{\phi x}$, that forms the same product will create the same level of systematic error in the perspective measurement.

As an example, assume that the misalignment of the mechanical x axis with respect to the translation is 10 milliradians (0.57 degrees), a value easily achieved with non-precision fabrication techniques. In this case, to achieve a perspective measurement to Class 1 accuracy (1 part in 1000 of the range) the allowable error in the rotation of the perspective measurement assembly is 71 milliradians, or 4.1 degrees. For Class 2 accuracy under the same conditions, the measurement of the rotation must be ten times more accurate.

G. Calibration of the Second Embodiment

In the referenced co-pending application, it was shown how to calibrate both the optical parameters of the borescope, and the relative alignment of the visual and translation coordinates. The assumption there was that the mechanical x axis was directed exactly along the translation direction or that there would be no rotation of the borescope. The alignment calibration determines the two alignment angles $\theta_z$, and $\theta_y$ of the translation with respect to the visual coordinate system.

Figure 14:
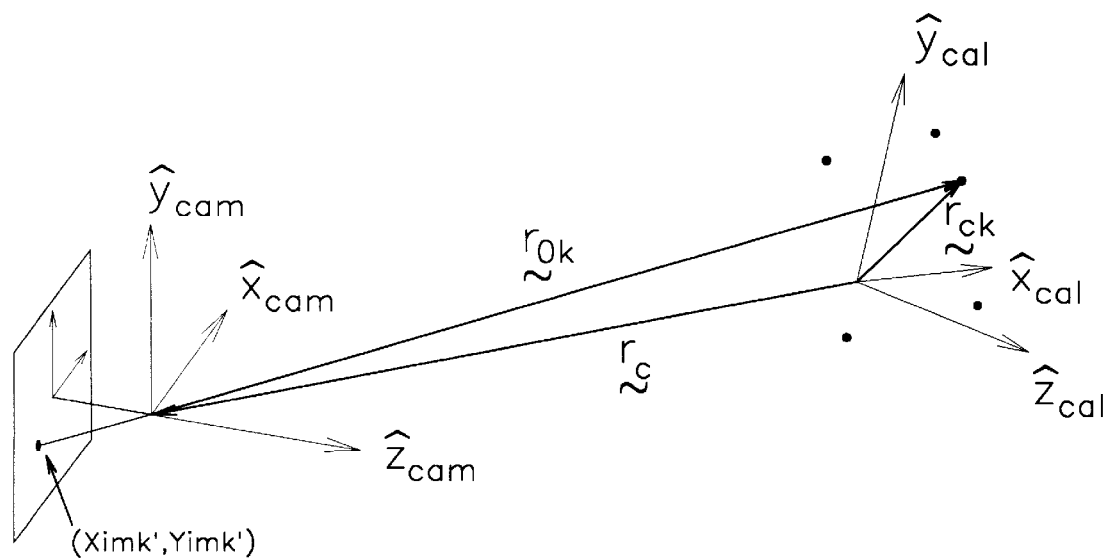
FIG. 14 depicts the calibration process for a perspective measurement system. It illustrates a group of calibration target points being viewed with a camera located at an unknown position and orientation.

In brief, calibration of the perspective measurement system requires that a field of calibration target points be viewed by the borescope. This process is depicted in FIG. 14. The calibration requires that the relative locations of all of the calibration points, $\vec{r}_{ck}$, be accurately known in some calibration coordinate system. As one result of the calibration process, the initially unknown location of the borescope nodal point in the calibration coordinate system, $\vec{r}_c$, is determined. As a second result, the rotation of the visual coordinate system with respect to the calibration coordinate system, represented by a composite rotation matrix $R_c$, is also determined.

If the borescope is translated from one viewing position to a second viewing position, and if the location of the nodal point is determined in the same calibration coordinate system at both positions, then the alignment of the displacement vector in the visual coordinate system can be determined as:

$$\vec{d}_v = R_c[r_c(\eta_2) - \vec{r}_c(\eta_1)] \quad (12)$$

where $\eta_1$ and $\eta_2$ are parameters denoting the translation position at the first and second viewing positions.

Equation (12) expresses the standard alignment calibration process which was fully disclosed in the aforementioned co-pending application. The result is specific to the particular orientation, $\theta_x$, that the perspective measurement assembly has during the alignment calibration, if the mechanical axis of rotation of the perspective measurement assembly is not aligned with the perspective displacement.

To perform the alignment calibration for the second embodiment of the improved system, this standard process is performed twice, with the perspective measurement assembly being rotated in the clamp of the BPA between these two alignment calibrations.

The preferred rotation between the two alignment calibrations is approximately 180 degrees. In other words, a standard alignment calibration is performed with, for instance, the calibration target array serving as the object of interest in FIG. 1. Then, the perspective measurement assembly is rotated 180 degrees inside the clamp of the BPA and the calibration target array is moved to the other side of the BPA so that the targets can again be viewed, and a second alignment calibration is performed.

In terms of the rotation angles defined in Equations (8) and (9) one can write the directions of the perspective displacements in the visual coordinates for these two alignment calibrations as:

$$\vec{d}_{uA} = \frac{\vec{d}_{vA}}{|\vec{d}_{vA}|} = R_z(\theta_z)R_y(\theta_y)R_x^{-1}(\phi_{x1})R_y^{-1}(\phi_y)R_z^{-1}(\phi_z)\begin{bmatrix}1\\0\\0\end{bmatrix} \quad (13)$$

$$\vec{d}_{uB} = \frac{\vec{d}_{vB}}{|\vec{d}_{vB}|} = R_z(\theta_z)R_y(\theta_y)R_x^{-1}(\phi_{x2})R_y^{-1}(\phi_y)R_z^{-1}(\phi_z)\begin{bmatrix}1\\0\\0\end{bmatrix}$$

In Equations (13) the known quantities are the rotation angles of the perspective measurement assembly $\phi_{x1}$ and $\phi_{x2}$ and the direction vectors $d_{uA}$ and $d_{uB}$ (which are known from use of Equation (12) as a result of the two individual alignment calibrations). The unknowns are the four alignment angles $\theta_z$, $\theta_y$, $\phi_z$, and $\phi_y$. Since the length of both direction vectors is fixed at unity, there are four independent equations in four unknowns.

Equations (13) can be rewritten as:

$$\vec{d}_{uA} = QR_x^{-1}(\phi_{x1})\vec{p} \quad (14)$$

$$\vec{d}_{uB} = QR_x^{-1}(\phi_{x2})\vec{p}$$

where matrix Q is a function of $\theta_z$ and $\theta_y$ and where vector p is a function of $\phi_z$ and $\phi_y$. The first equation can be solved for $\vec{p}$ to give:

$$\vec{p} = R_x(\phi_{x1})Q^{-1}\vec{d}_{uA} \quad (15)$$

and this can be substituted in the second equation to give:

$$\vec{d}_{uA} = QR_x^{-1}(\phi_{x2})R_x(\phi_{x1})Q^{-1}\vec{d}_{uB} \quad (16)$$

Equation (16) represents two non-linear equations in two unknowns. It can be solved for $\theta_z$ and $\theta_y$ by an iterative numerical procedure, such as Newton's method. In fact, (16) can be solved by a non-linear optimization process similar to those described in the referenced co-pending application.

Once these two angles are known, they can be substituted into Equation (15) to solve for $\phi_z$ and $\phi_y$. This latter solution is straightforward. The vector $\vec{p}$ can be written explicitly as:

$$\vec{p} = \begin{bmatrix}\cos(\phi_y)\cos(\phi_z)\\ \cos(\phi_y)\sin(\phi_z)\\ -\sin(\phi_y)\end{bmatrix} \quad (17)$$

so that the z component of $\vec{p}$ will give $\phi_y$ easily.

I note for completeness that one can also calibrate the second embodiment with a combination of mechanical and optical techniques. One can use the test rig of FIG. 9 to directly measure the angles $\phi_y$ and $\phi_z$ that the mechanical rotation axis makes with respect to the translation axis. When one does this, one is also inherently defining the specific orientation of the translation y and z axes, so that then one must set the zero point on protractor 670 to correspond with this specific orientation and also to define a plane which contains the optical axis of the borescope. Once these conditions have been satisfied, one then can use Equation (11) to determine the alignment angles $\theta_y$ and $\theta_z$ of the translation with respect to the visual coordinate system using standard alignment calibration data, in the same manner as was disclosed in the referenced co-pending application.

CONCLUSION, RAMIFICATIONS, AND SCOPE

Accordingly, the reader will see that the improved system of this invention solves the problem of routine alignment calibrations required with the perspective measurement system disclosed in my referenced co-pending application. The essence of the improvement is to provide for repeatably aligning the borescope with respect to the perspective displacement produced by the borescope positioning assembly while also allowing the borescope some freedom of motion in translation along and in rotation about its long axis. It has been shown that this can be achieved by adding a rotational reference surface to the borescope, and either accurately aligning the axis of this reference surface to the perspective displacement or measuring the rotation about that axis and taking that rotation into account in the perspective measurement procedure.

It is also the case that the improved system I have described is applicable to any single camera, linear motion embodiment of the perspective measurement system, if the camera is given a similar freedom to rotate about an axis which is not aligned with the linear motion. FIGS. 7, 12, and 13 apply just as well to this case as to the borescope/BPA embodiment discussed in detail. The same measurements, the same equations, and the same expanded alignment calibration as I have disclosed can be used to perform an accurate perspective measurement with such an embodiment.

Although the invention has been described with reference to particular embodiments, it will be understood by those skilled in the art that the invention is capable of a variety of alternative embodiments within the spirit and scope of the appended claims.

For example, one may use a pair of spherical bodies attached to and arranged so as to surround the borescope and disposed with some separation along its length, instead of the cylindrical calibration sleeve of my preferred embodiments. This structure would allow the borescope the required two degrees of motional freedom (when located in the V groove, but not clamped in position) and yet would provide the required orientation control when used in conjunction with the BPA.

It has been mentioned that there are any number of alternative groove shapes that can be used instead of my preferred V groove for the BPA reference surface. One could also use two separate short V grooves to locate the calibration sleeve, unlike the single long V groove of my preferred embodiments. In this case, the two V grooves would have to be accurately aligned with respect to each other, but this construction could save weight.

Another alternative would be to use a cylindrical reference surface on the BPA and a V groove mounted on the borescope. This would work just as well as the preferred embodiments in terms of the accuracy of the measurement. The disadvantage is that the centerline of the borescope would move with respect to the BPA as the borescope was rotated, thus making it more difficult to perform the measurement through a small inspection port as shown in FIG. 1.

The reference surface on the borescope does not have to be mounted over the lens tube, as it is in my preferred embodiments. Depending on the detailed construction of the individual borescope and on the need for a translational degree of freedom in the application, it is possible to provide the reference surface somewhere on the body of the borescope. The advantage is that there is then less of the length of the borescope lens tube dedicated to the support of the borescope, and thus more of the length is useable for reaching deep into an enclosure.

It is also possible to provide systems which have only the rotational degree of freedom, for those applications in which the depth of the object of interest is fixed. One simple example is that a specific region of the lens tube envelope could be marked as the region to be clamped into the BPA. If the borescope is always clamped at this same position, then there will be no change in alignment because of curvature of the lens tube envelope. This simple system is still subject to lack of repeatability in the alignment because of non-circularity of the lens tube, but it may be adequate for certain applications.

The system of using complementary reference surfaces to provide a repeatable relative alignment between a borescope and a borescope positioner could also be used with other, less complete, measurement systems which were known prior to the perspective measurement system to allow more flexibility in aligning the view to objects of interest.

I claim:

1. An apparatus for determining the locations of points on an object in three dimensions, said apparatus including a camera having an optical axis, and a support means, said support means providing a substantially straight axis of translation whereby said camera can be moved from a first viewing position to a second viewing position, said camera forming images of said points in an image plane, said optical axis being so arranged with respect to said axis of translation that there are created substantial shifts of said images in said image plane when said camera is moved between said first and second viewing positions, said apparatus also including image measurement means for measuring said shifts of said images and computing means which is adapted to compute said locations of said points using said shifts said images, wherein said support means also provides an axis of rotation, whereby said camera can also be rotated about said axis of rotation for alignment with objects of interest, said axis of rotation having an orientation with respect to said axis of translation, wherein the improvement comprises:

(a) means for measurement of an angle of rotation of said camera about said axis of rotation; and (b) means for incorporating said measurement of said angle of rotation into said determination of said locations of said points.

2. The apparatus of claim 1 wherein said means for measurement of an angle of rotation has a first portion which rotates with said camera and also has a second portion which is fixed to said support means.

3. The apparatus of claim 2 wherein said camera is a substantially side-looking rigid borescope.

4. The apparatus of claim 3 wherein said support means comprises a borescope positioning assembly and wherein said axis of rotation is defined by the engagement of a first reference surface attached to said borescope with a second reference surface attached to said borescope positioning assembly.

5. The apparatus of claim 4 wherein said first reference surface is a cylinder and said second reference surface is a V groove.

6. The apparatus of claim 5 wherein said borescope has a lens tube envelope and wherein said lens tube envelope has an outer surface and wherein said cylindrical first reference surface is said outer surface of said lens tube envelope.

7. The apparatus of claim 5 wherein said cylindrical first reference surface is a calibration sleeve attached to said borescope.

8. The apparatus of claim 1 wherein said means for incorporating said measurement of said angle of rotation into said determination of said locations includes calibration means for determining said orientation of said axis of rotation with respect to said axis of translation.

9. An apparatus for determining three-dimensional distances between points on an object, the determination of said distances having a maximum allowable error, said apparatus including a substantially side-looking rigid borescope, said borescope having an optical system containing a nodal point, said nodal point being located at a range from said object, wherein said borescope can be moved along a substantially straight translational axis from a first viewing position to a second viewing position, and wherein said borescope can also be rotated about a rotational axis for alignment with objects of interest, wherein the improvement comprises the arrangement of said rotational axis to be aligned parallel to said translational axis, the alignment having an allowable error, as expressed in radians, smaller than said allowable error in said determination of said three-dimensional distances, as expressed as a fraction of the range between said object and said nodal point.

10. The apparatus of claim 9 wherein said borescope is moved along said translational axis by a borescope positioning assembly and wherein said rotational axis is defined by the engagement of a first reference surface attached to said borescope with a second reference surface attached to said borescope positioning assembly.

11. The apparatus of claim 9 wherein said first reference surface is a cylinder and said second reference surface is a V groove.

12. The apparatus of claim 11 wherein said borescope has a lens tube envelope and wherein said lens tube envelope has an outer surface and wherein said cylindrical first reference surface is said outer surface of said lens tube envelope.

13. The apparatus of claim 11 wherein said cylindrical first reference surface is a calibration sleeve attached to said borescope.

14. A method of calibrating a perspective measurement system, wherein said system includes a camera which can be translated along a translational axis between a first viewing position and a second viewing position, thereby creating a perspective displacement, and wherein said camera can also be rotated about a rotational axis, and wherein an angle of rotation about said rotational axis is measured, and wherein said camera also includes a visual coordinate system, comprising the steps of:

(a) performing a first alignment calibration procedure with said camera rotated to a first angle of rotation, thereby determining the orientation of said perspective displacement in a first temporary visual coordinate system;

(b) performing a second alignment calibration procedure with said camera rotated to a second angle of rotation, thereby determining the orientation of said perspective displacement in a second temporary visual coordinate system; and (c) using said orientations of said perspective displacement in said first and second temporary visual coordinate systems, together with said first and second angles of rotation, to determine two angles of alignment of said rotational axis with respect to said translational axis and two angles of alignment of said visual coordinate system with respect to said rotational axis.

15. The method of claim 14 in which the angular difference between said first angle of rotation and said second angle of rotation is approximately 180 degrees.

* * * * *